US011622773B2

(12) United States Patent
Miller et al.

(10) Patent No.: US 11,622,773 B2
(45) Date of Patent: Apr. 11, 2023

(54) APPARATUS FOR FASTENING TISSUE AND OCCLUDING TUBULAR BODY STRUCTURES

(71) Applicant: Amsel Medical Corporation, Cambridge, MA (US)

(72) Inventors: Raanan Miller, Cambridge, MA (US); Nir Lilach, Kfar Yehoshua (IL)

(73) Assignee: AMSEL MEDICAL CORPORATION

( * ) Notice: Subject to any disclaimer, the term of this patent is extended or adjusted under 35 U.S.C. 154(b) by 305 days.

(21) Appl. No.: 16/382,944

(22) Filed: Apr. 12, 2019

(65) Prior Publication Data

US 2019/0231354 A1 Aug. 1, 2019
US 2021/0346027 A9 Nov. 11, 2021

Related U.S. Application Data

(63) Continuation-in-part of application No. 15/699,975, filed on Sep. 8, 2017, now Pat. No. 10,398,445, which
(Continued)

(51) Int. Cl.
*A61B 17/122* (2006.01)
*A61B 17/128* (2006.01)
(Continued)

(52) U.S. Cl.
CPC ...... *A61B 17/122* (2013.01); *A61B 17/12031* (2013.01); *A61B 17/1285* (2013.01);
(Continued)

(58) Field of Classification Search
CPC ............... A61B 17/0057; A61B 17/12; A61B 17/12009; A61B 17/122; A61B 17/128;
(Continued)

(56) References Cited

U.S. PATENT DOCUMENTS 6,312,446 B1 * 11/2001 Huebsch ............ A61B 17/0057
606/157
8,257,389 B2 * 9/2012 Chanduszko ...... A61B 17/0057
606/213
(Continued)

*Primary Examiner* — Martin T Ton
(74) *Attorney, Agent, or Firm* — Bookstein IP Law; Arthur Bookstein

(57) ABSTRACT

Apparatus and methods for occluding hollow body structures, such as blood vessels, and for attaching tissue layers together by providing implantable elements on opposite sides of the structure or tissue layers and drawing the implants together to occlude the body structure and/or bring the tissue layers together. The implants are deliverable in a low-profile configuration and self-expand to an enlarged configuration. The implantable elements are delivered by transfixing the body structure, then releasing the implants on opposite sides of the body structure and drawing the implants together to effect an occlusion or attachment. The implants are configured to apply oppositely directed forces to opposite surfaces of the tissue layers at alternate, circumferentially spaced locations and may constrain the tissue in a serpentine pattern or in a direct clamping pattern. The implants grip the tissue in a manner that defines a pressure zone about the transfixion aperture that prevents leakage from the aperture. The implants have a low profile in that they have a relatively short axial dimension relative to their deployed diameter.

12 Claims, 7 Drawing Sheets

Related U.S. Application Data is a continuation of application No. 15/438,924, filed on Feb. 22, 2017, now abandoned, which is a continuation-in-part of application No. 14/639,814, filed on Mar. 5, 2015, now Pat. No. 9,936,955, which is a continuation-in-part of application No. 14/272,304, filed on May 7, 2014, now Pat. No. 10,076,339, which is a continuation-in-part of application No. 13/857,424, filed on Apr. 5, 2013, now abandoned, application No. 16/382,944, which is a continuation-in-part of application No. 16/049,422, filed on Jul. 30, 2018, now Pat. No. 10,918,391, said application No. 13/857,424 is a continuation of application No. 13/348,416, filed on Jan. 11, 2012, now abandoned.

(60) Provisional application No. 62/408,426, filed on Oct. 14, 2016, provisional application No. 62/084,989, filed on Nov. 26, 2014, provisional application No. 61/948,241, filed on Mar. 5, 2014, provisional application No. 61/820,589, filed on May 7, 2013, provisional application No. 61/431,609, filed on Jan. 11, 2011.

(51) Int. Cl.
*A61B 17/12* (2006.01)
*A61B 17/00* (2006.01)
*A61B 17/34* (2006.01)
*A61B 17/04* (2006.01)

(52) U.S. Cl.
CPC ..... *A61B 17/12109* (2013.01); *A61B 17/3468* (2013.01); *A61B 2017/00407* (2013.01); *A61B 2017/00477* (2013.01); *A61B 2017/00867* (2013.01); *A61B 2017/0417* (2013.01); *A61B 2017/0462* (2013.01); *A61B 2017/12054* (2013.01)

(58) Field of Classification Search
CPC ...... A61B 17/1285; A61B 2017/00623; A61B 2017/12004
USPC .......................................................... 606/158
See application file for complete search history.

(56) References Cited

U.S. PATENT DOCUMENTS

| | | | |
|---|---|---|---|
| 2005/0267523 A1* | 12/2005 | Devellian | A61B 17/0057 606/213 |
| 2008/0208226 A1* | 8/2008 | Seibold | A61B 17/0057 606/158 |
| 2009/0084386 A1* | 4/2009 | McClellan | A61F 6/225 128/831 |
| 2013/0046331 A1* | 2/2013 | Christensen | A61B 17/1214 606/200 |

* cited by examiner

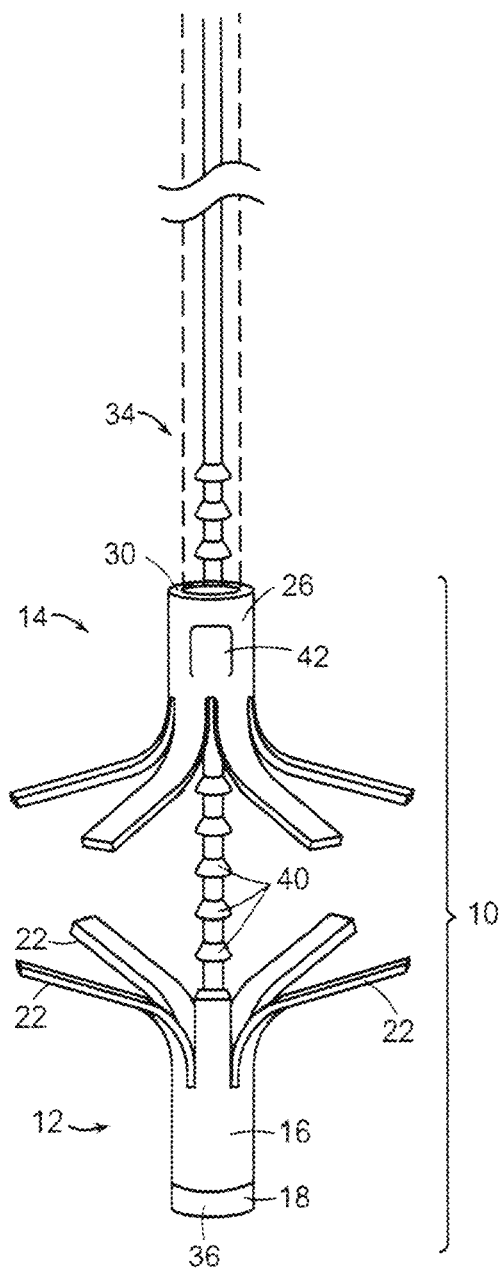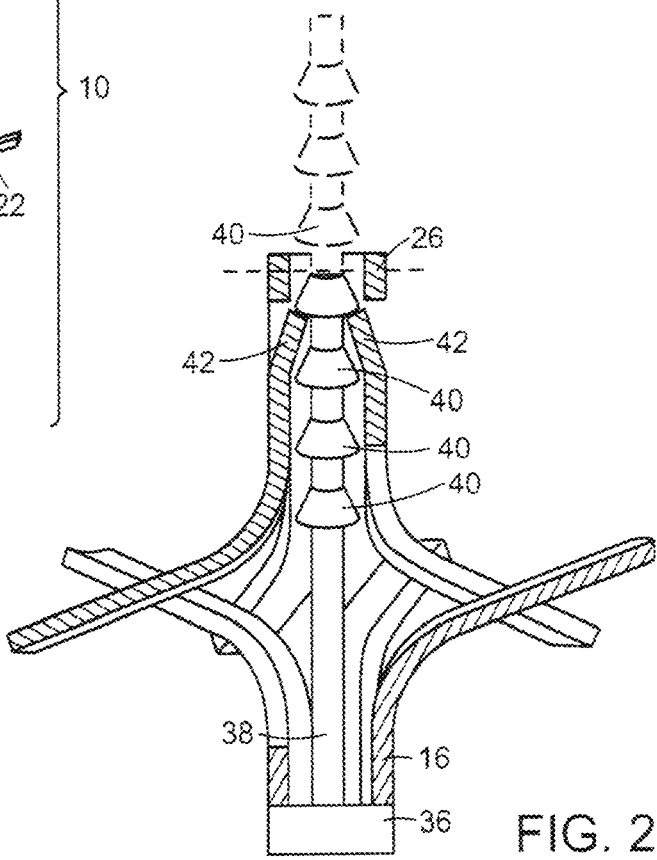
FIG. 1
FIG. 2

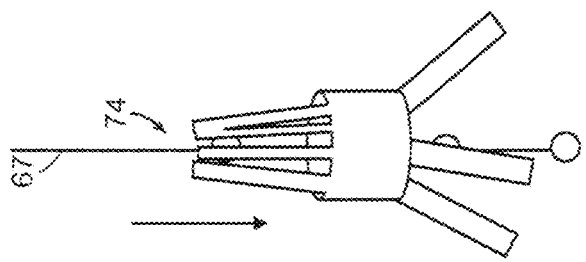
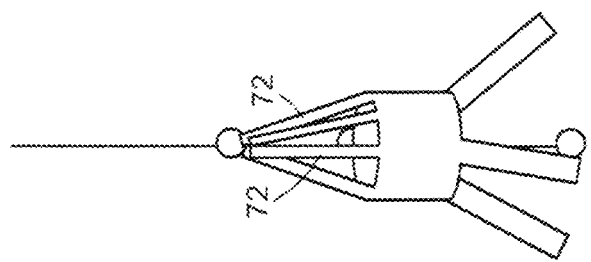
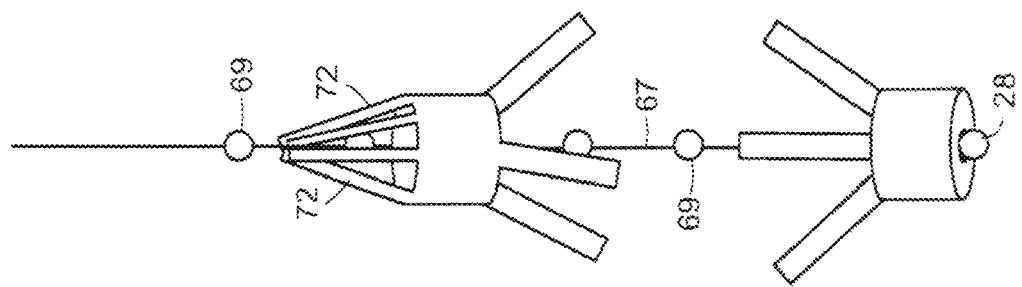
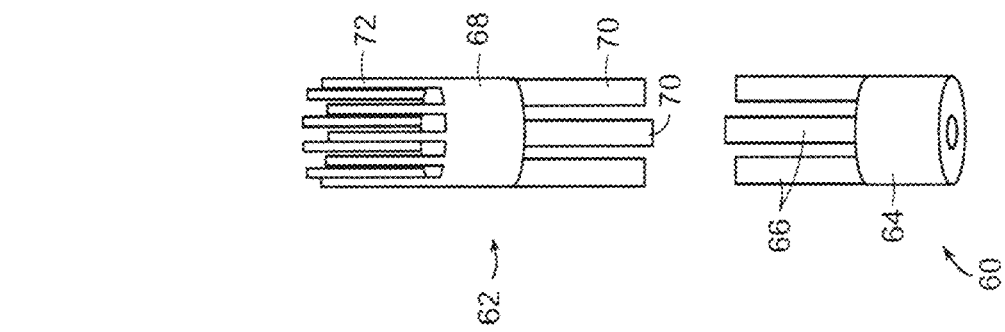

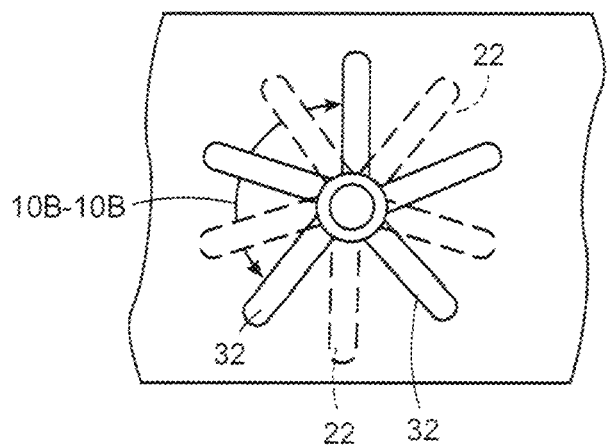
FIG. 10A
FIG. 10B
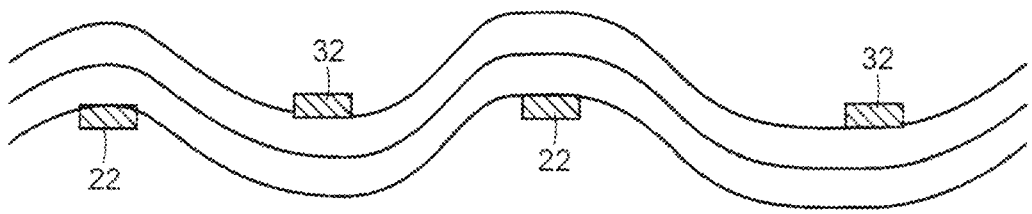
FIG. 11
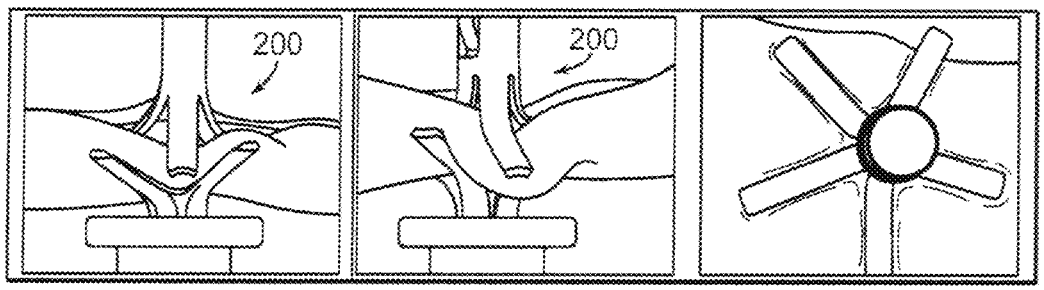

APPARATUS FOR FASTENING TISSUE AND OCCLUDING TUBULAR BODY STRUCTURES

REFERENCE TO PRIOR PATENT APPLICATIONS

This application is a continuation-in-part of U.S. patent application Ser. No. 15/699,975 filed Sep. 8, 2018 which
(i) is a continuation of U.S. patent application Ser. No. 15/438,924 filed Feb. 22, 2017 which
  (a) claims benefit of U.S. patent application Ser. No. 62/408,426, filed Oct. 14, 2016 filed Sep. 8, 2018
(ii) and is a continuation-in-part of U.S. patent application Ser. No. 14/639,814, filed Mar. 5, 2015 which
  (a) claims benefit of U.S. patent application Ser. No. 62/084,989, filed Nov. 26, 2014
(iii) and is a continuation-in-part of prior U.S. patent application Ser. No. 14/272,304, filed May 7, 2014, which
  (a) claims benefit of U.S. patent application Ser. No. 61/948,241, Mar. 5, 2014 and
  (b) claims benefit of U.S. patent application Ser. No. 61/820,589, filed May 7, 2013
(iv) and is a continuation-in-part of prior U.S. patent application Ser. No. 13/857,424, filed Apr. 5, 2013
(v) and is a continuation of U.S. patent application Ser. No. 13/348,416, filed Jan. 11, 2012
  (a) which claims benefit of U.S. patent application Ser. No. 61/431,609, filed Jan. 11, 2011.

The disclosures of the ten (10) above-identified patent applications are hereby incorporated by reference in their entireties as if fully set forth herein.

FIELD OF INVENTION

The invention relates to methods and devices for the occlusion of blood vessels and other tubular body structures and for clamping tissue layers together as well as to fasten tissue to non-tissue.

BACKGROUND

There are numerous medical conditions and procedures in which it is desirable or necessary to occlude hollow or tubular body organs such as, for example, blood vessels or to clamp together layers of tissue. One such example is in the treatment of venous complications, such as varicose veins, in which treatment involves selective occlusion of the veins. Other ducts, vessels or hollow body organs also may have to be obstructed or tissue layers clamped together for a variety of reasons. It would be desirable to provide devices and methods to effect occlusions of hollow body organs and to secure tissue layers to each other in a manner that that is easy and quick to apply and that has a low profile.

SUMMARY

The present invention provides a minimally invasive approach for occluding tubular body structures such as, for example, for treating varicose veins and other blood vessels where occlusion of the vessel or organ is an appropriate remedy.

More particularly, the inventions comprise the provision and use of a tissue clamp or fastener that may be used to occlude a vessel so as to restrict blood flow through the vessel or to secure tissue to other tissue or non-tissue structures. The device is configured to be deployed using visualization as may be provided by ultrasound and/or other visualization apparatus (e.g., CT, MRI, X-ray etc.). As a result, some procedures utilizing the invention may be provided in a physician's office with minimal local anesthetic and effectively no post-operative care. The invention also may be utilized in other procedures under direct visualization (e.g., during "open" surgery) or under indirect visualization such as during laparoscopic surgery where visualization is provided through the use of a scope, or during percutaneous surgery where visualization is provided through the use of imaging apparatus such as an ultrasound imager, an X-ray imager, etc.

In one form of the invention, there is provided a tissue fastener having two cooperative parts, including a distal component and a proximal components (referred to herein as "implants") each of which includes a plurality of legs configured to assume (i) a diametrically reduced configuration for disposition within the lumen of a deployment tube (e.g., a needle), and (ii) a diametrically expanded configuration in which the legs are extended radially to engage the target tissue (e.g., a blood vessel) such that when the deployed proximal and distal implants of the expanded fastener are brought together they can clamp tissue layers such as the walls of a vessel to occlude it. In one aspect of the invention the legs of the two are interdigitated when they brought together in the absence of tissue and, in another aspect, the opposing tissue layers are bought together by constraining them in a serpentine pattern characterized by a series of reversing bends that extend circumferentially about the fastener axis. In a further aspect of the invention a clamping or occlusion device is provided in which the tissue is transfixed but in which leakage of fluids (e.g., blood) from the transfixion puncture is minimized.

In yet another aspect of the invention, the two parts of the fastener, when secured together have a low profile and may be constructed to have an axial length that is less than the diameter defined by the expanded legs of the fastener The proximal and distal components of the fastener are deployed separately through a needle that is passed through tissue or other layers, first by deploying the distal fastener on the distal side of the tissue layers, then withdrawing the needle to the proximal side of the layers where the proximal implant is deployed. The implants are connected by a flexible, elongate filament-like retention member, the distal end of which end of which is secured too the distal implant with the proximal end extending proximally through the proximal implant, the needle and, if used, a delivery catheter or the like through which the apparatus is advanced to the target site. The filament has a plurality of protrusions formed along its length that cooperate with a detent on the proximal implant so that the proximal implant can be advanced along the filament in one direction, toward the distal implant. When the implants have been urged toward each other to clamp the tissue layers, the detent locks in engagement with one of the protrusions of the retention member to securely lock the implants together.

DESCRIPTION OF THE DRAWINGS

The various objects and advantages of the invention will be appreciated from the following description with reference to the accompanying drawings in which:

FIG. 1 is an isometric illustration of the proximal and distal implants of a two-part fastener of the invention with the legs of the implants being in their relaxed, expanded configuration;

FIG. 2 is sectional illustration of the proximal and distal implants locked together and with the legs of the implants interdigitated;

FIGS. 9A through 9D are diagrammatic, sequential illustrations of another embodiment of the invention;

FIG. 10A is a diagrammatic plan view of a fastener as seen from the proximal side in which the legs of the proximal and distal implants are out of registry with each other and are interdigitated;

FIG. 10B is a sectional illustration as seen along the circumferential line 10B of FIG. 10A showing the manner in which the interdigitated legs of the implants are oriented and the manner in which they constrain the tissue layers in a series of sequential alternating and reversing serpentine bends;

FIG. 11 is a series of three photographs illustrating a clamped, simulated blood vessel constrained in a serpentine pattern.

ILLUSTRATIVE EMBODIMENTS

Figure 3:
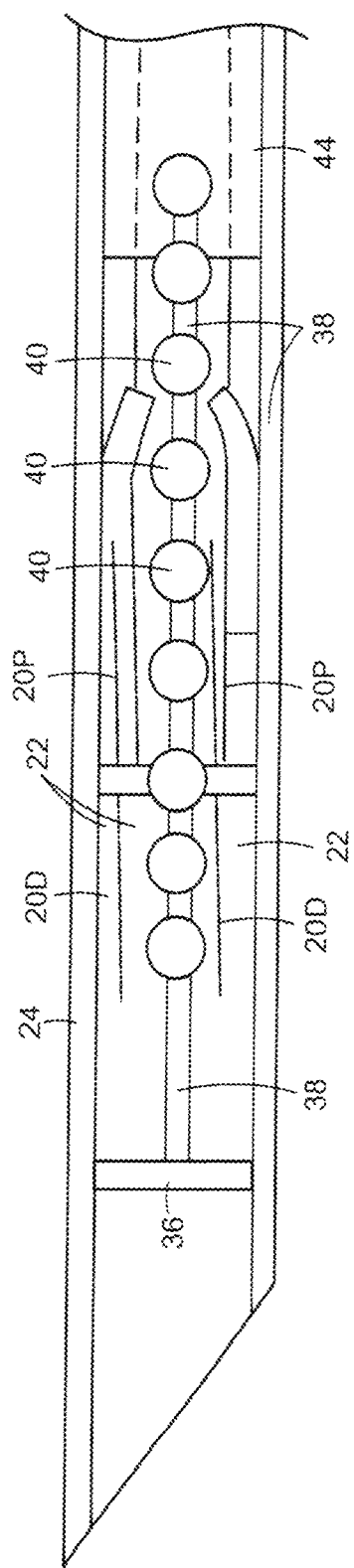
FIG. 3 is an enlarged cross section of a delivery needle with the proximal and distal implants arranged in tandem within the lumen of the needle and in readiness to be deployed.

FIG. 1 illustrates an embodiment of a two-part tissue fastener 10 formed in accordance with the present invention. Two-part fastener 10 generally comprises a distal implant 12 and a proximal implant 14. The fastener functions by pressing and securing tissue layers, such as the opposed walls of a blood vessel or other hollow anatomical structure together. In one illustrative embodiment, distal implant 12 may comprise a tubular body 16 having a distal end 18, a proximal end, and a lumen. The tubular body 16 is formed to have a plurality of longitudinally extending slits 20D (FIG. 3) that extend from a midportion of the body to the proximal end of the body and that define a plurality of segments that, when the body is in its expanded configuration will assume a plurality of radially extending legs 22. Distal implant body 16 preferably is formed out of an elastic material (e.g., a shape memory material having superelastic properties such as Nitinol or superelastic polymers, including superelastic plastics) and constructed so that the legs 22 normally are bent and project laterally away from the longitudinal axis of tube. They may be formed, for example, by laser cutting a Nitinol tube and shaping it under heat treatment as is well known in the art. Due to the elastic nature of the material used to form distal implant body 16, legs 22 can be deformed to a tubular, substantially linear, low profile shape (FIG. 3) so that they can be constrained within the lumen of a delivery tube or needle 24. However, when the constraint is removed, the elasticity of the material of the body 16 causes legs 22 to return to their relaxed, expanded position shown in FIG. 1.

FIGS. 1 and 2 also illustrate the proximal implant 14 that may comprise a tubular proximal body 26 having a distal end 28, a proximal end 30, and a lumen. Tube 26 is formed to have a plurality of slits 20P (FIG. 3) at its distal end to define a plurality of legs 32. One or more inwardly projecting detents 42 are formed in tube 26 adjacent its proximal end 30. Proximal implant 14 is preferably formed out of the same or similar material as the distal implant and is constructed so that its legs 32 normally project radially away from the longitudinal axis of tube 26 as shown. Legs 32 can be constrained inwardly to a low-profile configuration so that proximal implant 14 can assume a substantially tubular configuration along its length to be contained within the lumen of a delivery tube such as needle 24. However, when the constraint is removed, the elastic nature of the material causes legs 32 to return to their expanded positions.

The distal and proximal implants 12, 14 can be arranged so that the legs of one are interdigitated with the legs of the other which imposes a serpentine, clamping configuration on the tissue. Interdigitation refers to an arrangement that, when the proximal and distal implants are brought together the legs 32 of the proximal implant will overlie the spaces between the legs 22 of the distal implant (or vice versa), as discussed in further detail below. In order to bring the proximal and distal implants together and secure them with respect to each other, an elongate retention member 34 is provided and is secured to the distal implant. The retention member 34, may be flexible and may be filament-like, such as a suture or may be formed from a molded polymeric material. The distal end of the retention member 34 may be attached to the distal implant 12 in any of a number of ways, for example, if in the form of a suture it may be attached by passing the distal end of the suture through an opening in the distal end of the distal implant and a knot (suggested at 28 in FIG. 9B) may be tied to prevent the retention member 34 from being drawn through the opening. In a retention member formed from a molded polymer, the distal end of the member 34 may be formed to have a plug 36 that fits into or against the distal end 18 of the distal implant. This retention member 34 may be molded in the form of an elongate cord 38 integral with the plug 36 and having a plurality of longitudinally spaced protrusions 40 formed along its length. The retention member 34 extends proximally from the distal implant 12 through the proximal implant 14 and through the delivery tube 24 and delivery apparatus to a location where it can be accessed and controlled by a clinician. The retention member 34 cooperates with one or more detents 42 formed in the proximal implant 14 in a manner that allows the proximal implant to be advanced distally along the retention member 34 but precludes reverse movement. In other embodiments, the retention member may be fabricated so as to have some elasticity so that when the fastener 20 is deployed the retention member 34 may be stretched slightly so that its elasticity will bias the implants toward each other to enhance compression of the layers.

When the tissue layers are disposed between the proximal and distal implants and the implants are drawn together to fasten the layers, the cooperation between the detents and one of the protrusions locks the implants in that position. The detents 42 may take any number of configurations, for example, by forming one or more inwardly oriented tabs in the tubular body 26 of the proximal implant. The detents 42 and protrusions 40 should be formed so that the detents define a gap with respect to the dimensions and shape of the protrusions to permit the one-way movement of the proximal implant along the retention member described above. The protrusions may be formed in a variety of configuration, for example only, as conical shapes (FIGS. 1 and 2) or spheres (FIG. 3), each of which creates a wedging action as the protrusions pass through the detents, causing the protrusions or detents, or both, to deform enough to allow the protrusions to pass. In the form of detents shown (FIG. 2) the free ends of the tabs 42 extend radially inward sufficiently to prevent reverse movement of the protrusions thus locking the implants in position.

Among the advantages of the invention is that the fastener, when deployed has a relatively short axial dimension and a resulting low profile. The tubular bodies of the implants only need be long enough to provide support for the legs and contain one or more detents. When secured together no portion of either implant extends beyond the opposite end of the other implant. For example, with the present invention, the axial length of the connected implants measured from the distal end of the distal implant to the proximal end of the proximal implant may be no greater, and preferably less, than n the diameter defined by the radially expanded legs of the fastener 20.

Two-part fastener 20 may be deployed using associated installation apparatus shown, diagrammatically, in FIG. 3. The installation apparatus includes a needle 24 loaded with the proximal implant and distal implant 12, 14 in tandem and in readiness to be ejected from the needle 24. The retention member 34 extends through the proximal implant, the needle 24 and is long enough to enable the clinician to access and control the retention member from its proximal end. Additionally, the apparatus also includes a push tube 44 slidable within the needle and located proximally of the proximal implant 14. The implants 12, 14 and push tube 44 have the same outer diameter so as to fit slidably within the lumen of the needle 24 and to enable the push tube 44 to push the implants sequentially out of the distal end of the needle.

Figure 4:
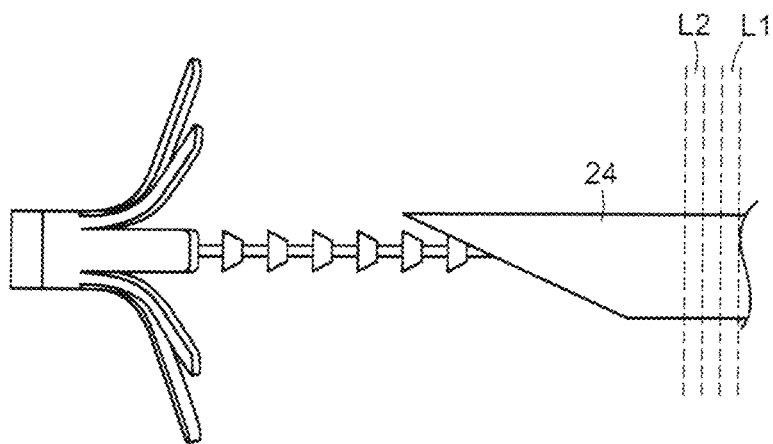
FIGS. 4, 5 and 6 are sequential, diagrammatic illustrations of the deployment of the fastener.
Figure 5:
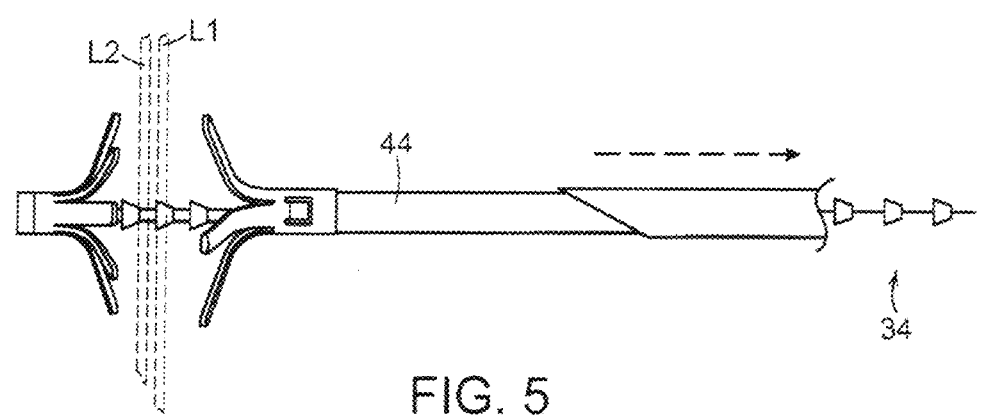
Figure 6:
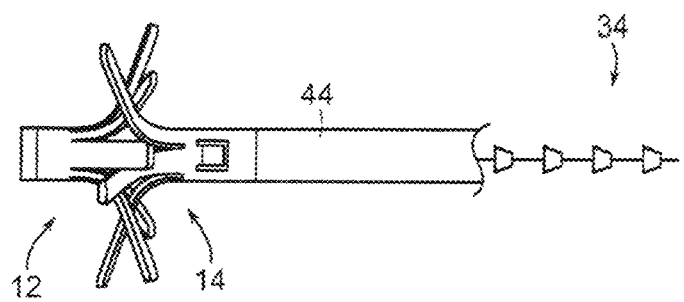

Two-part fastener 20 and its associated installation apparatus are used as follows. First, hollow needle 24 carrying the implants and push tube is passed through the skin of the patient, through intervening tissue, and across the blood vessel layers L1, L2 (FIGS. 4 and 5) that is to be occluded or through tissue layers to be fastened to position the distal outlet of the needle distally of the layers. Then the pusher tube 44 is advanced distally to push both implants distally enough to eject the distal implant 12 on the distal side of the tissue (FIG. 4), Upon ejection from the needle the legs 22 of the distal implant self-deploy to their expanded configuration. The needle containing the proximal implant and push tube then is retracted through the tissue to locate the distal end of the needle on the proximal side of the tissue (FIG. 5). Then, the pusher tube 44 is advanced distally to eject the proximal implant causing its legs 32 to self-deploy to their expanded configuration (FIG. 5). Next, while applying tension to the retention member 34, the pusher tube 44 is advanced distally against the proximal end of the proximal implant to cause the implants to be drawn together to clamp the tissue layers together (FIG. 6). As the proximal implant is advanced over the retention member the detent(s) 42 of the proximal implant can slip past the protrusions 40 on the retention member 34 but are precluded from reverse movement. It will be appreciated that the arrangement of the retention member with its protrusions that cooperate, ratchet-like, with the detent(s) provide an ability to draw the implants together to engage the tissues with a variable, desired degree of clamping force, the needle and pusher tube then can be retracted and the tail of the retention member proximal of the proximal implant can be severed. Thus, in the placement of the device the vessel or tissue is pierced (transfixed). Notwithstanding the transfixion, the interdigitated legs close the vessel or tissue to prevent flow and, therefore, there is no or minimal leakage of blood from the transfixion aperture. This may be contrasted with use of staples or sutures to occlude vessels or clamp tissue in which loss of blood through the puncture holes is a common problem.

In practicing the invention the legs of one or both of the implants may be arranged to extend at an acute angle to the longitudinal axis of the implant such that the legs on one or both of the implants collectively define a cone-like concave regions that face each other, as is apparent from FIGS. 1 and 2 and in which the legs are interdigitated. When tissue layers are clamped in this manner the layers are constrained in a serpentine configuration extending circumferentially about the longitudinal axis of the fastener. In an interdigitated arrangement, the legs of one of the implants are out of registry with those of the other implant so that when viewed in plan, the legs of one implant lie between the legs of the other. In particular, arranging the legs in an interdigitated array is considered to allow a tubular structure to be safely occluded in a way that avoids leakage problems associated with staples or conventional clips (e.g., hemoclips, Liga-clips, etc.). In an interdigitated configuration the opposing walls of the vessel are together partially wrapped about the legs 22, 32 in alternating directions to constrain the tissue in a serpentine configuration as seen diagrammatically in FIGS. 10A and 10B. Additionally, interdigitation provides an additional means by which the clamping forces can be adjustably controlled. By selecting a particular cone angle defined by the expanded legs, coupled with the dimensions of the legs, the characteristics of the serpentine pattern can be adjusted.

FIG. 11 shows three photographs of a two-part fastener 20 with interdigitated legs effectively clamping a simulated blood vessel. The interdigitated legs cause serpentine ripples, or folds, in the tissue that act to extend the effective closure, and causes closure of the vessel well beyond the region directly contacted by the fastener legs 22, 32. This is believed to result because the serpentine pattern extends radially somewhat beyond the periphery defined by the outer tips of the expanded implant legs. By way of example but not limitation, a two-part fastener 20 having a physical deployed diameter of 5.5 mm is able to close vessels that are over 7 mm (and even equal or greater than 1 cm) in diameter.

It should be understood that when an interdigitated device is locked into engagement with tissue, the thickness or nature of the tissue may cause the legs to flex to an extent that the degree of overlap is reduced or the legs may no longer overlap at all. Even when this occurs the legs of the proximal and distal implants still apply forces to the tissue that alternate in proximal and distal directions with the legs of the proximal implant applying distally directed forces and the legs of the distal implant applying proximally directed forces. With legs having sufficient stiffness these opposed forces of the implant legs, applied alternately at circumferentially spaced locations about the center of the fastener, are effective to secure tissue layers together or to occlude a lumen.

The legs 32, 22 of the proximal and distal implants 14, 12 may be beveled (or rounded) so that they do not present sharp edges, and legs 32, 22 may be designed to separate slightly from the tissue at the free end of each leg. This is in order to minimize any catching or damage that may be imparted on the tissue by legs 22, 32, whereby to minimize tearing or ripping of the tissue. Legs 22, 32 may be provided with smooth surfaces or may be roughened, as by chemical etching or mechanical means, so as to enhance the imaging reflectivity of the implants, or to provide increase tissue capture and gripping.

The two-part fastener as described may be configured to occlude blood vessels under fluid pressures of at least 100 mm Hg and up to 300 mm Hg. Fasteners also may be made that are capable of resisting pressure of over 700 mm Hg.

Figure 12:
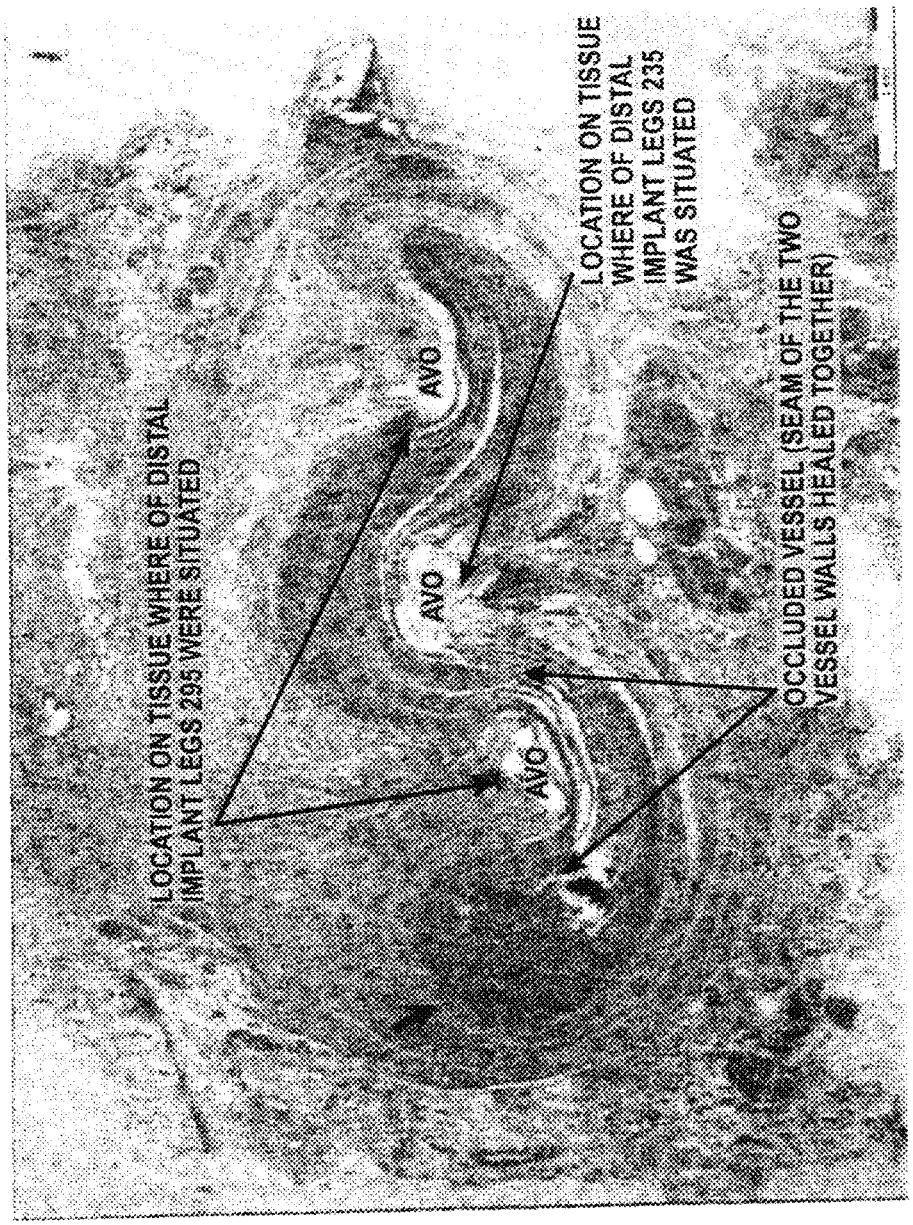
FIG. 12 is a histological photograph of a blood vessel occluded with an interdigitated fastener and illustrating the serpentine pattern in which the walls of the vessel were constrained.

When the two-part fastener is arranged with its legs interdigitated, the wall thickness of the vessel to be occluded or the tissue layers to be joined does not necessarily determine whether an effective occlusion or attachment can be achieved. As long as the interdigitation of the legs constrains the vessel walls in a serpentine pattern or the forces are alternately applied in proximal and distal directions circumferentially about the center of the fastener, the walls of the vessel may be brought into contact with each other sufficiently to occlude the vessel, even when the legs 22 and legs 32 may not cross each other's plane ("overlap") regardless of the summed wall thickness of the vessel. Thus, vessels and tissue layers of varying dimensions can be effectively occluded or fastened. Whether and to what extent the legs of the proximal and distal implants may overlap will depend on the characteristics and dimensions of the anatomy to be occluded and the configuration for the implants necessary to constrain the tissue in a serpentine configuration.

Where legs 32, 22 of the proximal and distal implants 14, 12 are interdigitated, the serpentine constraint of the tissue layers reduces the force needed to occlude the vessel and is considered to be much less than the force needed to close the same vessel with a conventional ligation clip. FIG. 12 is a photograph of a histological section of tissue from a vessel occluded with an interdigitated fastener and showing the serpentine pattern of the tissue layers of the vessel walls after healing of up to 30 days. The vessel is completely occluded and the vessel wall tissue is compressed and adhered to itself in the serpentine configuration. The "pie crust" or serpentine closure may be observed more clearly as well. The arrow indicates the collapsed undulating artery. AVO indicates the location of the interdigitating legs of two-part fastener 20.

The two-part fastener 20 of the present invention may be used to occlude vessels, ducts and/or to compress tissue so it is occluded/compressed at forces less than 700 grams, while the force required to seal off vessels or clamp tissue with a commercially available Ligaclip are about ten times greater. The two-part fastener 20 of the present invention can maintain operation within the range of elasticity of the material and does not need to be plastically deformed to realize occlusion.

Figure 7:
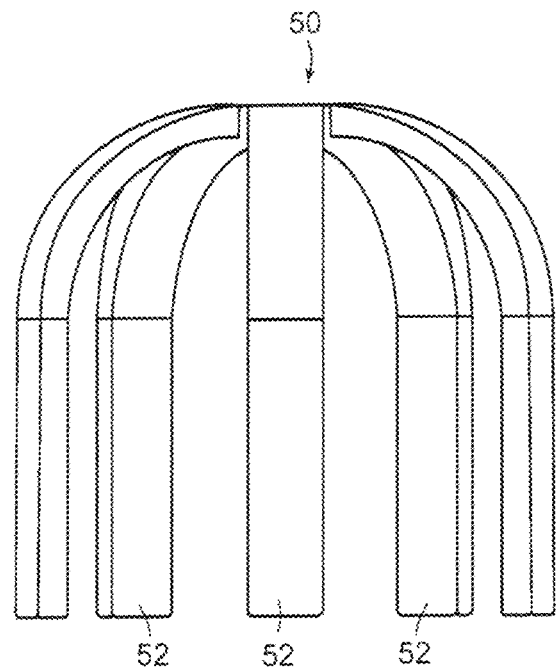
FIG. 7 is a side view illustrating another embodiment of the invention.
Figure 8:
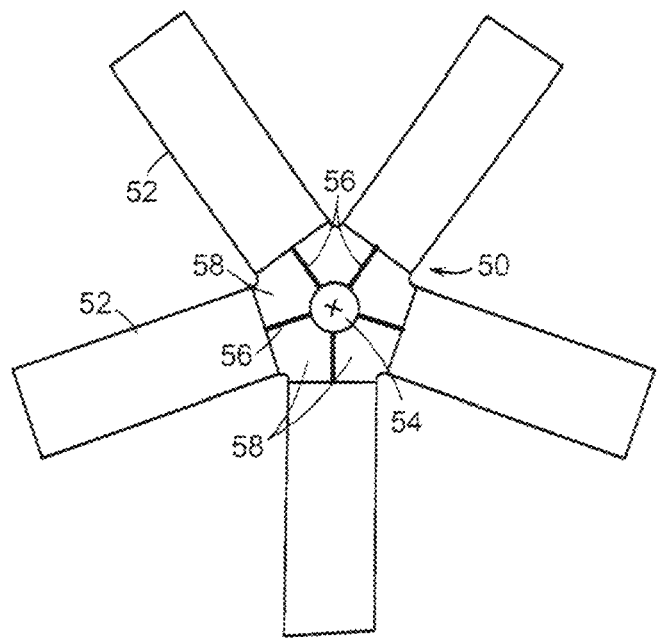
FIG. 8 is an end view of the embodiment of FIG. 8 as seen from the top of FIG. 8.

FIGS. 7 and 8 illustrate, diagrammatically, an individual proximal implant that may be made in another embodiment of the invention. In this embodiment, the implant may be formed from a flat sheet of heat treatable, shape memory, elastic material (e.g., Nitinol) and may be laser cut from the sheet in what may be in a spider-like configuration having a central portion 50 and a plurality of legs 52 extending radially outward from the central portion. The central portion 50 may have a central aperture 54 and a plurality of slits 56 that extend radially outward from the aperture 54 to define a plurality of tabs 58, the inner ends of which are free and define the aperture 54. The device then is heat treated while maintaining it in a desired shape, for example, as the concave, conical shape described above in connection with the embodiment of FIG. 1. FIG. 7 shows this embodiment with the legs 52 constrained in parallel so that the implant can be contained in a delivery tube, such as a needle. The distal implant (not shown) in this embodiment may be formed in the same manner. In this embodiment, a retention member also is employed and secured to the distal implant in a manner similar to that described above. The retention member, with protrusions, extends from the distal implant proximally through the central aperture 54 to a proximal location where the clinician can access it. The tabs 58 are flexible so that they can flex to allow the protrusions on the retention member to pass through as the proximal implant is advanced distally.

FIGS. 9A-9D illustrate, diagrammatically, a modified embodiment of the invention and the sequence of its operation. In this embodiment, a distal implant 60 and a proximal implant 62, are provided and may be formed in the same manner as described above. The distal implant 60 has a tubular body 64 with a plurality of proximally extending legs 66 arranged as described above and which can be constrained to fit in a delivery tube or needle. As with the previously described embodiments, a retention member 67 having longitudinally spaced protrusions 69 is secured to the distal implant and extends in a proximal direction. The proximal implant 62 has a tubular body 68 and a plurality of distally extending legs 70 arranged in a manner as described above such that when deployed and brought together the legs of the proximal and distal implants may interdigitate. The proximal implant 62 also is provided with a plurality of fingers or tabs 72 that extend from the proximal end of the tubular body 68. The fingers 72 are arranged so that their free ends converge as suggested in FIGS. 9B and 9C to cooperate to define a narrow opening 74 through which the retention member may pass (FIG. 9D). The free ends of the fingers are configured so that the narrow opening is smaller than the protrusions on the retention member. The fingers 72, however, are flexible and can flex as a proximal implant is advanced distally over the protrusions in a distal direction (FIG. 9D), allowing the protrusions to pass through the opening. Once a protrusion has passed through the opening, backward movement is prevented because the protrusion abuts the distal tips of fingers (FIG. 9C).

It will be appreciated that the fasteners of the present invention can also be used to occlude tubular and hollow structures other than blood vessels. By way of example but not limitation, the temporary fastener of the present invention can be used to occlude fallopian tubes, vas deferens, ducts, as the bile duct and cystic ducts for cholecystectomy, lymphatic vessels, including the thoracic duct, fistula tracts, etc. The present invention can also be used to bring, attach and/or connect at least two folds (e.g., two sides of the stomach, or other parts of the legs, etc.) together so that they are connected.

In addition to occluding blood vessels the fasteners can be used for clamping and compressing regions of resected organs so as to reduce or stop blood flow or blood loss after surgery. For example, the fastener may be used in solid organ resection of the kidney or liver or other organs. Blood loss and secretion leakage (e.g., bile, urine, etc.) can be problematic in existing solid organ resection procedures. Average blood loss for a liver resection is 700-120 ml. By clamping desired regions of the solid organ with one or more fasteners, it is possible to significantly reduce the amount of undesirable fluid loss (blood loss, secretion leakage, etc.). The fastener can be used to apply pressure selectively to broad areas of the organ and, additionally, may also be used to close off selective tubular structures and vessels connecting the organ with other regions of the body. Multiple discrete fastener elements may be deployed across regions of the organ. Where multiple, single, separate puncture placements of the fastener are used, different regions of the solid organ may be compressed to different and controllable degrees.

Although described in the context of occluding blood vessels, the present invention may be practiced under direct visualization (e.g., during "open" surgery) or under indirect visualization (e.g., during laparoscopic surgery where visualization is provided through the use of a scope, or during percutaneous surgery where visualization is provided through the use of imaging apparatus such as an ultrasound imager, an X-ray imager, etc.).

The present invention can also be used to connect tissue with other non-tissue materials, e.g., graft materials, hernia meshes, drug delivery materials, etc.

In each of the foregoing embodiments the transfixion aperture that is formed by the delivery needle does not tend to leak blood (or other fluid) because the zone about the point of transfixion where the legs cooperate to prevent fluid flow substantially prevents fluid from reaching the aperture. Thus, the invention may be advantageous in many situations over other techniques in which blood loss may be problematic (e.g., staples, sutures, etc.)

Thus, it will be appreciated that the foregoing description provides devices and methods for occluding vessels and for clamping tissue layers that provide advantages over prior art techniques. Fasteners and clamps are provided that employ a pair of components that are brought together on opposite sides of a vessel or tissue layers to compress the vessel walls or tissue layers. The clamping may be directly on the tissue or may be such as to constrain the tissue layers in a serpentine pattern that is considered to occlude or clamp with less direct compressive force on the tissue. Applying oppositely directed forces at alternating locations on the tissue circumferentially about the center of the fastener also may effect occlusion or clamping. The fasteners may include pluralities of radially extending legs or spirally oriented elements that cooperate to effect occlusion or clamping. In each instance a pressure zone of occlusion is formed about the point of transfixion to prevent leakage through the transfixion aperture. Moreover, these advantages are achieved in devices that have a low profile.

It should be understood, however, that the foregoing description of the invention is intended merely to be illustrative and that other embodiments, modification and equivalents may be apparent to those skilled in the art without departing from the principles of the invention.

The invention claimed is:

1. An apparatus for securing a layer of tissue to another layer of tissue or non-tissue, each layer having an inwardly facing surface and an outwardly facing surface, the apparatus comprising:
   a hollow delivery tube having a distal outlet, the tube being advanceable transversely through an aperture formed in each of the layers;
   a distal implant contained in the delivery tube comprising a distal body and a plurality of legs which may assume (i) a diametrically-reduced delivery configuration and (ii) a diametrically-expanded deployed configuration in which the legs are extended radially of the distal body; and
   a proximal implant contained in the delivery tube, separate from the distal implant, the proximal implant comprising a proximal body and a plurality of legs configured to assume (i) a diametrically-reduced delivery configuration and (ii) a diametrically-expanded deployed configuration in which the legs are extended radially of the proximal body;
   each of the implants being deployable out of the delivery tube separately and independently of and in spaced relation to each other with the deployed legs of the proximal and distal implants being disposed on opposite sides of the layers with the outwardly facing surfaces of the layers disposed between and facing the deployed legs of the implants;
   an elongate retention member attached to the distal body, the retention member having a plurality of longitudinally spaced protrusions formed along its length, the retention member extending through the proximal body, the proximal body being movable, as a unit, along the retention member toward the distal implant;
   the proximal implant having at least one detent formed in its body, the detent being engageable with the protrusions on the retention member and being configured to allow the proximal implant to move, as a unit, along the retention member toward the distal implant but to prevent movement along the member in a proximal direction whereby the relative positions and proximity of the implants can be adjusted;
   the deployed legs of the implants being configured to constrain the layers disposed between the legs in a serpentine configuration that circumscribes the bodies of the implants;
   whereby, the distal implant may be deployed distally of one of the layers and the proximal implant may thereafter be separately deployed proximally of another layer with the retention member extending through the apertures and transfixing the layers;
   whereby, with layers disposed between the deployed implants, the proximal implant can be advanced, as a unit, along the retention member to clamp and secure the layers between the legs of the deployed implants.

2. The apparatus as defined in claim 1 wherein when the implants are drawn fully together in the absence of the layers, the deployed legs of the proximal and distal implants are interdigitated.

3. The apparatus as defined in claim 2 further comprising:
   each of the implants having an axis and wherein the legs of at least one of the implants being configured so that when deployed they assume an acute angle with respect to the axis.

4. The apparatus as defined in claim 3 wherein the legs of each of the implants assumes an acute angle when deployed, each set of legs defining a concavity, the concavities of the implants facing each other.

5. The apparatus as defined in claim 1 wherein each of the implants has an axis, the apparatus further comprising:
   the combined axial length of the deployed implants, when brought into engagement with each other along the retention member and in the absence of tissue between the implants, being no greater than about the diameter of the deployed legs.

6. The apparatus as defined in claim 1 wherein the at least one detent comprises:
   a tab formed in a part of the tubular body of the proximal implant, the tab having a free end that protrudes into the lumen of the proximal body and extends in a proximal direction, the free end of the tab defining a gap with an opposing portion of the tubular body, the gap presenting a slight interference fit with the protrusions of the retention member, at least one of the tab or the protrusions being yieldable to permit movement of the proximal implant along the retention member only in a distal direction.

7. The device as defined in claim 1 wherein the retention member is elastic whereby the implants may be biased toward each other when deployed to fasten tissue.

8. An apparatus for securing a layer of tissue to another layer of tissue or non-tissue, each layer having an inwardly facing surface and an outwardly facing surface, the apparatus comprising:
- a hollow delivery tube having a distal outlet, the tube being advanceable transversely through an aperture formed in each of the layers;
- a distal implant contained in the delivery tube comprising a distal body and a plurality of legs which may assume (i) a diametrically-reduced delivery configuration and (ii) a diametrically-expanded deployed configuration in which the legs are extended radially of the distal body; and
- a proximal implant contained in the delivery tube, separate from the distal implant, the proximal implant comprising a proximal body and a plurality of legs configured to assume (i) a diametrically-reduced delivery configuration and (ii) a diametrically-expanded deployed configuration in which the legs are extended radially of the proximal body;
- each of the implants being deployable out of the delivery tube separately and independently of and in spaced relation to each other with the deployed legs of the proximal and distal implants being disposed on opposite sides of the layers with the outwardly facing surfaces of the layers disposed between and facing the deployed legs of the implants;
- an elongate retention member attached to the distal body, the retention member having a plurality of longitudinally spaced protrusions formed along its length, the retention member extending through the proximal body, the proximal body being movable, as a unit, along the retention member toward the distal implant;
- the proximal implant having at least one detent formed in its body, the detent being engageable with the protrusions on the retention member and being configured to allow the proximal implant to move, as a unit, along the retention member toward the distal implant but to prevent movement along the member in a proximal direction whereby the relative positions and proximity of the implants can be adjusted;
- whereby, the distal implant may be deployed distally of one of the layers and the proximal implant may thereafter be separately deployed proximally of another layer with the retention member extending through the apertures and transfixing the layers;
- whereby, with layers disposed between the deployed implants, the proximal implant can be advanced, as a unit, along the retention member to clamp and secure the layers between the legs of the deployed implants;
- the delivery tube comprising a needle having a sharp distal end adapted to form the apertures in the layers;
- each leg in each of the implants having a free end;
- the proximal and distal implants being slidably contained in the lumen of the needle, in tandem relation and in their delivery configurations, with the distal implant located distally of the proximal implant and with the free ends of the legs of the implants facing each other;
- a pusher tube slidably disposed in the needle proximally of the proximal implant and adapted to engage the proximal end of the proximal implant to push the proximal and distal implants toward the distal outlet of the needle;
- the retention member extending through and beyond the proximal implant and pusher tube to a proximal location;
- whereby the loaded delivery needle can be advanced through the layers to locate the outlet distally of the layers, the pusher tube then can be advanced to cause the distal implant to be ejected from the outlet and deploy, then the needle can be retracted to position the outlet proximally of the layers and the pusher tube can then be advanced distally to eject the proximal implant from the outlet, whereupon the pusher tube can be advanced distally along the retention member to urge the proximal implant toward the distal implant to cause the implants to clamp the layers together.

9. An apparatus for securing a layer of tissue to another layer of tissue or non-tissue comprising:
- a distal implant formed from a flat, unitary sheet of shape memory material and comprising a central portion and a plurality of legs extending radially of and unitary with the central portion, the legs being configured to assume (i) a diametrically-reduced delivery configuration in which it can be passed through the layers and (ii) a diametrically-expanded deployed configuration in which the legs are extended radially of the distal body; and
- a proximal implant, separate from the distal implant, and formed from a unitary flat sheet of shape memory material and comprising a central portion having an aperture formed therein and a plurality of legs extending radially of and unitary with the central portion, the legs being configured to assume (i) a diametrically-reduced delivery configuration in which it can be passed through the layers and (ii) a diametrically-expanded deployed configuration in which the legs are extended radially of the distal body;
- an elongate retention member attached at one end to the central portion of the distal body, the retention member having a plurality of longitudinally spaced protrusions formed along its length, the retention member extending through an aperture in the central portion of the proximal body;
- the central portion of the proximal implant having a plurality of radial slits extending radially outward of the aperture, the slits defining a plurality of tabs having free ends that define the aperture, the aperture presenting slight interference fit to the protrusions, the degree of interference being such as to enable the protrusions and aperture to enable the proximal implant to be advanced along the retention member but to resist reverse movement when the implants are in clamping engagement with the layers;
- each of the implants being deployable separately and independently of the other implant;
- the distal implant being deployable distally of one of the layers and the proximal implant being deployable proximally of another layer, the deployed implants being spaced apart with the retention member transfixing the layers;
- whereby, with layers disposed between the deployed implants, the proximal implant can be advanced along the retention member to clamp and secure the layers between the legs of the implants;
- wherein when the implants are drawn fully together in the absence of the layers, the deployed legs of the proximal and distal implants are interdigitated.

10. The apparatus as defined in claim 9 further comprising:

each of the implants having an axis and wherein the legs of at least one of the implants being configured so that when deployed they assume an acute angle with respect to the axis.

11. The apparatus as defined in claim 10 wherein the legs of each of the implants assumes an acute angle when deployed, each set of legs defining a concavity, the concavities of the implants facing each other.

12. An apparatus for securing a layer of tissue to another layer of tissue or non-tissue comprising:
- a distal implant formed from a flat, unitary sheet of shape memory material and comprising a central portion and a plurality of legs extending radially of and unitary with the central portion, the legs being configured to assume (i) a diametrically-reduced delivery configuration in which it can be passed through the layers and (ii) a diametrically-expanded deployed configuration in which the legs are extended radially of the distal body; and
- a proximal implant, separate from the distal implant, and formed from a unitary flat sheet of shape memory material and comprising a central portion having an aperture formed therein and a plurality of legs extending radially of and unitary with the central portion, the legs being configured to assume (i) a diametrically-reduced delivery configuration in which it can be passed through the layers and (ii) a diametrically-expanded deployed configuration in which the legs are extended radially of the distal body;
- an elongate retention member attached at one end to the central portion of the distal body, the retention member having a plurality of longitudinally spaced protrusions formed along its length, the retention member extending through an aperture in the central portion of the proximal body;
- the central portion of the proximal implant having a plurality of radial slits extending radially outward of the aperture, the slits defining a plurality of tabs having free ends that define the aperture, the aperture presenting slight interference fit to the protrusions, the degree of interference being such as to enable the protrusions and aperture to enable the proximal implant to be advanced along the retention member but to resist reverse movement when the implants are in clamping engagement with the layers;
- each of the implants being deployable separately and independently of the other implant;
- the distal implant being deployable distally of one of the layers and the proximal implant being deployable proximally of another layer, the deployed implants being spaced apart with the retention member transfixing the layers;
- whereby, with layers disposed between the deployed implants, the proximal implant can be advanced along the retention member to clamp and secure the layers between the legs of the implants;
- the deployed legs of the implants being configured to constrain the layers disposed between the legs in a serpentine configuration that circumscribes the bodies of the implants.

* * * * *